US010786453B2

(12) United States Patent
Deshayes et al.

(10) Patent No.: US 10,786,453 B2
(45) Date of Patent: Sep. 29, 2020

(54) 10-HYDROXYSTEARIC ACID COMPOSITIONS

(71) Applicant: DSM IP ASSETS B.V., Heerlen (NL)

(72) Inventors: Cyrille Deshayes, Kaiseraugst (CH); Christine Mendrok-Edinger, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/092,514

(22) PCT Filed: Mar. 29, 2017

(86) PCT No.: PCT/EP2017/057423
§ 371 (c)(1),
(2) Date: Oct. 10, 2018

(87) PCT Pub. No.: WO2017/178235
PCT Pub. Date: Oct. 19, 2017

(65) Prior Publication Data
US 2019/0160006 A1 May 30, 2019

(30) Foreign Application Priority Data

Apr. 13, 2016 (EP) .................................. 16164998

(51) Int. Cl.
| A61K 9/107 | (2006.01) |
| A61K 31/20 | (2006.01) |
| A61K 47/08 | (2006.01) |
| A61K 8/365 | (2006.01) |
| A61K 8/37 | (2006.01) |
| A61Q 7/00 | (2006.01) |
| A61Q 19/00 | (2006.01) |
| A61K 8/49 | (2006.01) |
| A61K 8/39 | (2006.01) |
| A61K 8/86 | (2006.01) |
| A61K 8/60 | (2006.01) |
| A61K 8/06 | (2006.01) |
| A61K 8/34 | (2006.01) |
| A61K 8/35 | (2006.01) |
| A61K 8/40 | (2006.01) |
| A61K 9/00 | (2006.01) |
| A61K 47/10 | (2017.01) |
| A61K 47/14 | (2017.01) |
| A61K 47/16 | (2006.01) |
| A61Q 17/04 | (2006.01) |

(52) U.S. Cl.
CPC .............. *A61K 9/107* (2013.01); *A61K 8/062* (2013.01); *A61K 8/342* (2013.01); *A61K 8/35* (2013.01); *A61K 8/365* (2013.01); *A61K 8/37* (2013.01); *A61K 8/375* (2013.01); *A61K 8/39* (2013.01); *A61K 8/40* (2013.01); *A61K 8/4973* (2013.01); *A61K 8/602* (2013.01); *A61K 8/604* (2013.01); *A61K 8/608* (2013.01); *A61K 8/86* (2013.01); *A61K 9/0014* (2013.01); *A61K 31/20* (2013.01); *A61K 47/08* (2013.01); *A61K 47/10* (2013.01); *A61K 47/14* (2013.01); *A61K 47/16* (2013.01); *A61Q 7/00* (2013.01); *A61Q 19/00* (2013.01); *A61K 2800/30* (2013.01); *A61K 2800/49* (2013.01); *A61Q 17/04* (2013.01)

(58) Field of Classification Search
CPC ................................ A61K 8/062; A61K 8/362
See application file for complete search history.

(56) References Cited

U.S. PATENT DOCUMENTS

| 6,190,680 B1 * | 2/2001 | Sakurada ............. A23D 7/0053 424/401 |
| 8,048,456 B2 * | 11/2011 | Burke-Colvin ........ A61K 8/585 424/725 |
| 8,883,838 B2 * | 11/2014 | Shanler ................ A61K 9/0014 514/401 |
| 2009/0324505 A1 | 12/2009 | Seidling et al. |
| 2012/0157528 A1 | 6/2012 | Pehratovic et al. |

FOREIGN PATENT DOCUMENTS

| JP | 2009-286739 | 12/2009 |
| KR | 10-1556362 | 10/2015 |
| WO | 2007/039057 | 4/2007 |
| WO | 2016/059169 | 4/2016 |

OTHER PUBLICATIONS

Schroepfer, Jr., "Stereospecific Conversion of Oleic Acid to 10-Hydroxystearic Acid", The Journal of Biological Chemistry, vol. 241, No. 22, pp. 5441-5447, Nov. 25, 1966.
International Search Report for PCT/EP2017/057423, dated Jun. 30, 2017, 4 pages.
Written Opinion of the ISA for PCT/EP2017/057423, dated Jun. 30, 2017, 7 pages.
Database WPI, XP-002759199, 2 pages.

* cited by examiner

*Primary Examiner* — Kyle A Purdy
(74) *Attorney, Agent, or Firm* — Nixon & Vanderhye P.C.

(57) ABSTRACT

The present invention relates to topical compositions comprising 10-hydroxystearic acid or a salt thereof and at least one nonionic emulsifier. The present invention also relates to a method to retard or inhibit the re-crystallisation of 10-hydroxystearic acid or a salt thereof in a topical composition, said method comprising formulating 10-hydroxystearic acid or a salt thereof in the presence of at least one nonionic emulsifier.

19 Claims, No Drawings

10-HYDROXYSTEARIC ACID COMPOSITIONS

This application is the U.S. national phase of International Application No. PCT/EP2017/057423 filed 29 Mar. 2017, which designated the U.S. and claims priority to EP Patent Application No. 16164998.3 filed 13 Apr. 2016, the entire contents of each of which are hereby incorporated by reference.

The present invention relates to topical compositions comprising 10-hydroxystearic acid or a salt thereof and at least one nonionic emulsifier. The present invention also relates to a method to retard or inhibit the recrystallisation of 10-hydroxystearic acid or a salt thereof in a topical composition, said method comprising formulating 10-hydroxystearic acid or a salt thereof in the presence of at least one nonionic emulsifier.

Hydroxy fatty acids such as 10-hydroxystearic acid (CAS: 638-26-6) have been reported to have beneficial cosmetic effects in treating or preventing any symptoms caused by negative developments of the physiological homeostasis of healthy skin, as well as for the promotion of hair growth and protection from hair loss. However, none of these compounds have been developed into commercial products because of difficulties in establishing product forms in which the active remains soluble over time and does not recrystallize upon storage.

Thus, there is an ongoing need to overcome the drawbacks of the prior art and to find a robust and stable emulsion system which allows the incorporation of 10-hydroxystearic acid without the formation of crystals upon storage.

Surprisingly it has been found that the recrystallization of 10-hydroxystearic acid can be significantly retarded or even inhibited by using at least one nonionic emulsifier.

Thus, in a first embodiment the invention relates to topical compositions comprising 10-hydroxystearic acid or a salt thereof and at least one nonionic emulsifier, with the proviso that the composition is free of isobutylparaben.

The amount of 10-hydroxystearic acid or a salt thereof in the topical compositions according to the invention is advantageously selected in the range of 0.001 to 5 wt.-%, preferably in the range of 0.01 to 3 wt.-%, most preferably in the range of 0.1 to 2 wt.-%, such as in particular in the range of 0.1 to 1.5 wt.-%, based on the total weight of the composition.

The amount of the nonionic emulsifier in the topical compositions according to the invention is advantageously selected in the range of 0.1 to 7 wt.-%, preferably in the range of 1 to 6 wt.-%, most preferably in the range of 1 to 5 wt.-%, based on the total weight of the composition.

10-Hydroxystearic acid (CAS: 638-26-6) can e.g. prepared as illustrated by G. Schroepfer in Biological Chemistry (1966), 241(22), 5441-7 and has the following formula:

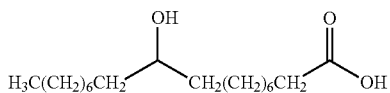

Both enantiomers may be used according to the present invention, and the preferred enantiomeric form is the (R)-10-hydroxystearic acid.

The salt may be formed by reaction with an organic base, or an alkali or earth alkaline base resulting in the respective salt. Suitable bases which release a cosmetically acceptable cation that is not toxic to the skin and/or does not cause allergic reactions are well known to a person skilled in the art. Examples of organic salts are the respective ammonium and alkyl ammonium salts such as in particular the triethanolammonium salts. Preferred alkali or earth alkali salts are the respective lithium, sodium, potassium, magnesium or calcium salts.

Nonionic emulsifiers to be used according to the present invention employed in cosmetics are well known to a person skilled in the art.

Particularly suitable nonionic surfactants for the purpose of the present invention are the esters of fatty alcohols, polyalkylenglycol alkyl ethers, polyalkyleneglycol fatty acid esters, glucoside alkyl ethers, alkyl glucose esters, glycerol alkyl esters, sorbitan fatty acid esters as well as block polymers of polyethylene glycol and polypropylene glycol.

The term 'alkyl' encompasses straight chain and branched alkyl groups. Preferably the term 'alkyl' refers to straight chain $C_1$-$C_{28}$ alkyl groups and branched $C_3$-$C_{28}$ alkyl groups, more preferably to straight chain $C_1$-$C_{28}$ alkyl groups, most preferably to $C_1$-$C_{22}$ alkyl groups.

The term 'fatty alcohol' respectively 'fatty acid' refers to alcohols, respectively acids with a long aliphatic chain, which is either saturated or unsaturated and may also be branched.

Preferably, and if not defined otherwise, the term 'fatty alcohol' respectively 'fatty acid' refers to saturated or unsaturated, straight chain or branched $C_{12}$-$C_{28}$, preferably $C_{12}$ to $C_{22}$ alcohols respectively carboxylic acids. In a particular preferred embodiment, the term 'fatty alcohol' respectively 'fatty acid' refers to saturated or unsaturated, straight chain $C_{12}$-$C_{28}$, preferably $C_{12}$ to $C_{22}$ alcohols respectively carboxylic acids.

Particularly suitable esters of fatty alcohols for the purpose of the present invention encompass fatty acid ester of fatty alcohols such as in particular $C_{12}$-$C_{22}$-alkylester of $C_{12}$-$C_{22}$-alcohols. Particularly suitable esters of fatty alcohols for the purpose of the present invention are the esters of cetearyl alcohol and fatty acids derived from (hydrogenated) olive oil or $C_{16}$-$C_{18}$-alkyl esters of $C_{16}$-$C_{18}$ and $C_{18}$-unsaturated alcohols.

Particularly suitable polyalkylen glycol alkyl ethers for the purpose of the present invention are polyethylene glycol alkyl ether (PEG-ether), which are e.g. obtainable by etherifying the respective polyethylene glycol with a fatty alcohol. The number of ethylene oxide monomers in the polyethylene chain is typically selected in the range of 2 to 150, more preferably in the range of 2 to 50, most preferably in the range of 2 to 30. Thus, particular advantageous PEG-ethers to be used in all embodiments of the present invention encompass polyethyleneglycol $C_{12}$-$C_{22}$-alkyl ether having an ethylenoxide number of 2 to 30 such as steareth-2, steareth-21, Laureth-4, Laureth-7, coceth-7 and ceteareth-12. Most preferred PEG-ethers in all embodiments of the present invention are polyethyleneglycol $C_{18}$-alkyl ether having an ethylenoxide number of 2 to 30 such as steareth-2 and steareth-21.

Particularly suitable of polyalkylene glycol fatty acid esters for the purpose of the present invention are the polyethylene glycol fatty acid esters (PEG-esters), which are e.g. obtainable by esterifying the respective polyethylene glycol with a fatty acid. The number of ethylene oxide monomers in the polyethylene chain is typically selected in the range of 2 to 150, more preferably in the range of 10 to 110, most preferably in the range of 20 to 100. Thus, particular advantageous PEG-esters to be used in all embodiments of the present invention encompass the polyethylene glycol $C_{12}$-$C_{22}$ fatty acid esters having an ethylenoxide number of 2 to 150 such as in particular PEG-20 Stearate, PEG-40 stearate, PEG-100 stearate, PEG-40 hydrogenated castor oil, PEG-40 castor oil, PEG-30 dipolyhydroxystearate, PEG-30 glyceryl stearate and PEG-7 glyceryl cocoate. Most preferred PEG-esters in all embodiments of the present invention are the polyethylene glycol stearates having an ethylenoxide number of 10 to 110 such as in particular PEG-40 stearate and PEG-100 stearate.

Particularly suitable glucoside alkyl ethers for the purpose of the present invention are decyl glucoside, lauryl glucoside, octyl glucoside and cetearyl glucoside.

Particularly suitable alkylglucose esters for the purpose of the present invention are (polyglyceryl) alkylglucose alkyl ester such as the alkylglucose alkyl ester methyl glucose sesquistearate or the polyglyceryl alkylglucose alkyl ester polyglyceryl-3 methylglucose distearate.

Particularly suitable glycerol alkyl esters for the purpose of the present invention are the glycerol (mono- or di-) $C_{12}$-$C_{22}$ fatty acid esters which are obtainable by esterification of glycerin and the respective $C_{12}$-$C_{22}$ fatty acid such as in particular glyceryl laurate or glyceryl stearate as well as the esterification products of polyglycerin and a $C_{12}$-$C_{22}$ fatty acid such as e.g. polyglyceryl-6 distearate.

Particularly suitable sorbitan fatty acid ester for the purpose of the present invention are sorbitan (mono-, di- or tri-) fatty acid esters which can be prepared by esterification of sorbitan with a fatty acid. Particular suitable sorbitan fatty acid esters are the fatty acid mono esters of sorbitan (e.g. commercially available under the tradename SPAN) such as sorbitan sesquioleate, sorbitan isostearate and sorbitan trioleate or esters of sorbitan and (hydrogenated) olive oil fatty acids (chemical name: D-Glucitol, 1,4-anhydro-, 6-monoester with olive oil fatty acids, e.g. commercially available under the tradename sorbitan olivate) or sorbitan stearate (e.g. commercially available as Arlatone 2121) as well as polyethoxylated sorbitan ester (e.g. commercially available under the tradename Tween).

Particular suitable block polymers of polyethylene glycol and polypropylene glycol for the purpose of the present invention are the alkyl PEG/PPG which are the reaction product of an alkyl alcohol and one or more equivalents each of ethylene oxide and propylene oxide (forming repeats of polyethylene glycol (PEG) and polypropylene glycol (PPG), respectively). Preferred alkyl alcohols are fatty alcohols such as in particular $C_{12}$-$C_{22}$-alkylalcohols. Exemplary ether of block polymers of polyethylene glycol and polypropylene glycol encompass PPG-1-PEG-9 lauryl glycol ether and PPG-1-PEG-9 lauryl glycol ether. Further suitable block polymer of polyethylene glycol and polypropylene glycol for the purpose of the present invention are the polymers made from dimethicone and polyoxyethylene and polyoxypropylene such as e.g. PEG/PPG-18/18 dimethicone and cetyl PEG/PPG-10/1 dimethicone.

In a preferred embodiment the at least one nonionic emulsifier is selected from the group consisting of $C_{12}$-$C_{22}$-alkylester of $C_{12}$-$C_{22}$-alcohols, polyethylene glycol alkyl ethers such as more preferably polyethylene glycol $C_{12}$-$C_{22}$-alkyl ether having an ethylenoxide number of 2 to 30, polyethylene glycol fatty acid esters such as more preferably polyethylene glycol $C_{12}$-$C_{22}$ fatty acid esters having an ethylenoxide number of 2 to 150, (polyglyceryl) alkylglucose alkyl esters, glycerol $C_{12}$-$C_{22}$ fatty acid estesr and sorbitan mono fatty acid esters.

In a most preferred embodiment, the at least one nonionic emulsifiers according to the present invention is selected from the group consisting of polyglyceryl-3 methylglucose distearate (CAS 187339-62-4, e.g. commercially available as TEGO® Care 450), cetearyl glucoside (CAS 246159-33-1, e.g. commercially available as TEGO® Care CG 90), methyl glucose sesquistearate (CAS 68936-95-8) which is e.g. commercially available as TEGO Care PS), cetearyl olivate (CAS 348616-34-2), sorbitan olivate (CAS 223706-40-9), the mixture of cetearyl olivate and sorbitan olivate is e.g. commercially available as Olivem®1000, PEG-40 stearate (CAS 9004-99-3) which is e.g. commercially available as Myrj™ S40, PEG-100 stearate (CAS 9004-99-3), glyceryl stearate (CAS 123-94-4), the mixture of PEG-100 stearate and glyceryl stearate is e.g. commercially available as Arlacel™ 165 or Simulsol 165, steareth-2 (CAS 9005-00-9 (Generic)/16057-43-5) which is e.g. commercially available as Brij™ S2 and steareth-21 (CAS 9005-00-9 (Generic)) which is e.g. commercially available as Brij™ S721, as well as mixtures thereof.

In another advantageous embodiment, the present invention relates to topical compositions wherein the at least one nonionic emulsifier is selected from the group of PEG-ethers or PEG-esters with all the definitions and preferences as given above, optionally in combination with an anionic emulsifier such as e.g. stearic acid as the use of these PEG-emulsifiers leads to particularly good results.

The topical compositions according to the present invention are free of isobutyl paraben, more preferably, however, the compositions are free of any paraben such as in particular free of methylparaben, ethylparaben, propylparaben, and butylparaben.

In another preferred embodiment, the topical compositions according to the present invention are also free of a cooling agent and/or an exothermic agent.

The term 'cooling agent' is well known to a person skilled in the art and refers to cosmetic ingredients which generate a cooling sensation on the skin such as 1-menthol, and menthol derivatives (e.g. menthyl Ruguri glyceryl ether, menthyl lactate, 1-menthyl 3-hydroxybutyrate, menthyl salicylate, menthone), dl-camphor, eugenol, mint, and eucalyptus.

The term 'exothermic agent' refers to components which generate heat upon mixing with water, such as for example calcium chloride, magnesium chloride, aluminum chloride, ferric chloride, zinc chloride, calcium sulfate, magnesium sulfate, zinc sulfate, aluminum sulfate, ferrous sulfate, calcium carbonate, and sodium carbonate.

The topical compositions according to the present invention preferably contain additionally a co-emulsifier. Particular preferred co-emulsifiers according to the present invention are nonionic solid fatty alcohols having from 12 to 22 carbon atoms as well as mixtures thereof such as preferably lauryl alcohol, myristyl alcohol, pentadecyl alcohol, cetyl alcohol, heptadecyl alcohol, stearyl alcohol, isostearyl alcohol, palmitoleyl alcohol as well as mixtures thereof. Particular preferred co-emulsifiers are behenyl alcohol which is e.g. commercially available as Lanette 22 from BASF, cetyl alcohol which is e.g. commercially available as Lanette 16 from BASF and cetearyl alcohol (i.e. a mixture of cetyl- and stearyl alcohol), which is e.g. commercially available as Lanette® O from BASF.

The amount of co-emulsifier in the topical compositions according to the present invention is preferably selected in the range of 0.1 to 20 wt.-%, more preferably in the range of 0.5 to 10 wt.-%, most preferably in the range of 1 to 5 wt.-%, based on the total weight of the composition.

In a particular advantageous embodiment of the invention the at least one nonionic emulsifier is selected from the group consisting of polyglyceryl-3 methylglucose distearate, cetearyl glucoside, cetearyl olivate, sorbitan olivate, methyl glucose sesquistearate, PEG-100 stearate, glyceryl stearate, steareth-2 and steareth-21 as well as mixtures thereof and the co-emulsifier is selected from the group consisting of cetyl alcohol, behenyl alcohol and cetearyl alcohol as well as mixtures thereof.

In another embodiment, the present invention relates to a method to retard or inhibit the re-crystallisation of 10-hydroxystearic acid or a salt thereof in a topical composition, said method comprising formulating 10-hydroxystearic acid or a salt thereof in the presence of a nonionic emulsifier with all the preferences and definitions given above.

The term "topical composition" as used herein refers in particular to cosmetic compositions that can be topically applied to mammalian keratinous tissue such as e.g. human skin or hair, particularly human skin.

The term "cosmetic composition" as used in the present application refers to cosmetic compositions as defined under the heading "Kosmetika" in Rompp Lexikon Chemie, 10th edition 1997, Georg Thieme Verlag Stuttgart, New York as well as to cosmetic preparations as disclosed in A. Domsch, "Cosmetic Preparations", Verlag für chemische Industrie (ed. H. Ziolkowsky), $4^{th}$ edition, 1992.

Preferably, the topical preparations according to the present invention are in the form of an emulsion or micro emulsion (in particular of O/W-type), PIT-emulsion, multiple emulsion (e. g. O/W/O-type and W/O/W) or pickering emulsion.

In all embodiments of the present invention the topical compositions according to the present invention are preferably emulsions comprising an aqueous phase and an oily phase, most preferably the topical compositions are O/W emulsions. Preferably, the aqueous phase constitutes at least 50 wt.-% and the oily phase at least 10 wt.-% of the composition. In particular the water phase constitutes at least 60 wt.-% and the oily phase constitutes less than 40 wt.-%. In particular the water phase constitutes at least 70 wt.-% and the oily phase constitutes less than 30 wt.-% of the composition. Most preferably, the amount of the water phase is selected in the range of 70-90 wt.-% and the amount of the oily phase is selected in the range of 10-30 wt.-%, based on the total weight of the composition.

It is well understood, that the water phase and the oily phase together form the emulsion, wherein, however, minor amounts (up to 5 wt.-%) of remainder ingredients such as preservatives, active, fragrances, etc. may also be present which may be added to one of the phases or separately e.g. at end of the preparation which is well known to a person skilled in the art.

Particular suitable oil components and solvents to form the oily phase of the topical compositions according to the present invention encompass: Ethanol; Triethylhexanoin; Glycols such as propylene glycol, propylene glycol dibenzoate, butylene glycol, pentylene glycol and PPG-15 ethoxydiglycol stearyl ether; Dialkylethers such as dicaprylyl ether, PPG-3 myristyl ether; Esters of saturated and/or unsaturated, branched and/or unbranched alkanecarboxylic acids having a chain length of 3 to 30 carbon atoms and saturated and/or unsaturated, branched and/or unbranched alcohols having a chain length of 3 to 30 carbon atoms, or from esters of aromatic carboxylic acids and saturated and/or unsaturated, branched and/or unbranched alcohols having a chain length of 3 to 30 C atoms such as e.g. isopropyl myristate, isopropyl palmitate, isopropyl oleate, n-butyl stearate, n-hexyl laurate, n-decyl oleate, isononyl isononanoate, 2-ethylhexyl palmitate, ethylhexyl benzoate, $C_{12-15}$ alkyl benzoate, 2-hexyl decyl stearate, oleyl oleate, erucyl oleate, erucyl erucate, propylene glycol dicaprylate/dicaprate, diisopropyl adipate, isoamyl laurate, octyldodecyl neopentanoate, di-$C_{12}$-$C_{13}$ alkyl tartrate and synthetic, semi-synthetic and natural mixtures of such esters such as e.g. jojoba oil; Carbonates such as dicaprylyl carbonate; Triglycerides such as caprylic/capric triglyceride, PEG-8 caprylic/capric triglycerides; Silicone oils; Straight or branched chain hydrocarbons having from 8-20 carbon atoms, such as decane, dodecane, tridecane, tetradecane, and $C_{8-20}$ isoparaffins; Natural oils and fats (including butters) derived from animal, vegetable, or mineral sources such as e.g. almond oil, apricot kernel oil, argan oil, avocado butter, avocado oil, cocoa butter (theobroma oil), camelina oil, canola oil, carrot seed oil, castor oil, citrus seed oil, coconut oil, corn oil, cottonseed oil, cucumber oil, egg oil, grapeseed oil, hemp seed oil, jojoba oil, lanolin oil, linseed oil, macadamia nut oil, meadowfoam seed oil, mineral oil, mink oil, olive oil, palm kernel oil, peach kernel oil, peanut oil, rapeseed oil, rose hip oil, safflower oil, sesame oil, shark liver oil, shea butter, soybean oil, sunflower seed oil, sweet almond oil, tallow (beef) oil, tallow (mutton) oil, turtle oil, vegetable oil, and wheat germ oil and as well as mixtures of these oil components and solvents.

Particularly suitable oil and solvent components to form the oil phase of the topical composition according to the present invention are isopropyl palmitate, caprylic/capric triglyceride, PPG-15 stearyl ether, butylene glycol, dicaprylyl carbonate, dicaprylyl ether, di-$C_{12}$-$C_{13}$ alkyl tartrate, diisopropyl adipate, triethylhexanoin, propylene glycol dicaprylate/dicaprate, isoamyl laurate, octyldodecyl neopentanoate, ethylhexyl benzoate, pentylene glycol, PEG-8 caprylic/capric triglycerides, propylene glycol dibenzoate, PPG-3 myristyl ether, ethoxydiglycol, $C_{12-15}$ alkyl benzoate and ethanol as well as mixtures thereof.

The water phase advantageously consists essentially of water, a moisturizer and a thickener. Suitable thickeners encompass e.g. xanthan gum such as e.g. available as Keltrol CG-RD, guar-gum, alginate, polyacrylates, polyquaternium, silicone-based polymers, carbomers, acrylates/C10-30 alkyl acrylates copolymers, hydroxyethylcellulose, ammonium acryloyldimethyltaurate/VP copolymer as well as other acryloyldimethyl taurate copolymers. Preferred thickeners are xanthan gum or acrylates/C10-30 alkyl acrylates copolymers or polyacrylic acid (INCI: Carbomer).

According to the invention xanthan gum is preferably used in low concentrations such as e.g. in concentrations selected in the range of 0.05-1 wt.-%, preferably in the range of 0.05-0.3 wt.-%, based on the total weight of the topical composition.

According to the invention acrylates/C10-30 alkyl acrylates is preferably used in low concentrations such as e.g. in concentrations selected in the range of 0.05-1 wt.-%, preferably in the range of 0.05-0.3 wt.-%, based on the total weight of the topical composition.

According to the invention polyacrylic acid is preferably used in low concentrations such as e.g. in concentrations selected in the range of 0.05-1 wt.-%, preferably in the range of 0.05-0.3 wt.-%, based on the total weight of the topical composition.

A particularly suitable moisturizer is glycerine, but not limited to. Other moisturizers that can applied are: e.g. saccharide isomerate such as e.g. available as Pentavitin®, penthylene glycol such as e.g. available as Hydrolite®, propylene glycol, butylene glycol, urea, among others.

According to the invention glycerin is preferably used in low concentrations such as in concentrations selected in the range of 0.5-10 wt.-%, more preferably in the range of 1-6 wt.-%, based on the total weight of the topical composition.

Particular suitable preservatives to be used in the topical compositions according to the invention are phenoxyethanol, ethylhexyl glycerine, potassium sorbate and sodium benzoate as well as mixtures thereof.

According to the invention the preservative (total amount) is preferably used in low concentrations such as in concentrations selected in the range of 0.1-3 wt.-%, more preferably in the range of 0.5-2 wt.-%, most preferably in the range of 015 to 1 wt.-%, based on the total weight of the topical composition.

Topical compositions in accordance with the invention can be in the form of a liquid, lotion, a thickened lotion, a gel, a cream, a milk, an ointment or paste, and can be optionally be packaged as an aerosol and can be provided in the form of a mousse such as an aerosol mousse, a foam or a spray foam, a spray, a stick.

The topical compositions according to the invention may optionally be combined with further cosmetically active ingredients such as ingredients for skin lightening; tanning prevention; treatment of hyperpigmentation and/or cellulite; preventing or reducing acne, wrinkles, lines, atrophy and/or inflammation; slimming (e.g. phytanic acid), firming, moisturizing, energizing, self-tanning, soothing, as well as agents to improve elasticity and skin barrier. It's well known to a person skilled in the art that the cosmetically active ingredients useful herein can in some instances provide more than one benefit or operate via more than one mode of action.

If present, the additional cosmetically active ingredient is typically included in an amount of at least 0.001 wt. %, based on the total weight of the topical preparation. Generally, an amount of about 0.001 wt. % to about 30 wt. %, preferably from about 0.001 wt. % to about 10 wt. %, based on the total weight of the topical composition of an additional cosmetically active agent is used.

The topical cosmetic compositions of the invention can also contain usual cosmetic adjuvants and additives, such as preservatives/antioxidants, fatty substances/oils, water, organic solvents, silicones, thickeners, softeners, emulsifiers, sunscreens, antifoaming agents, aesthetic components such as fragrances, surfactants, fillers, sequestering agents, chelating agents, anionic, cationic, nonionic or amphoteric polymers or mixtures thereof, propellants, acidifying or basifying agents, dyes, colorings/colorants, abrasives, absorbents, essential oils, skin sensates, astringents, pigments or nanopigments, e.g. those suited for providing a photoprotective effect by physically blocking out ultraviolet radiation, or any other usual cosmetic adjuvant or additive usually formulated into cosmetic compositions.

Active ingredients as well as cosmetic adjuvants and additives commonly used in the skin care industry and which are suitable for their use in the compositions of the present invention are e.g. described in the CTFA Cosmetic Ingredient Handbook, Second Edition (1992) without being limited thereto.

The necessary amounts of the active ingredients as well as cosmetic adjuvants and additives can—based on the desired product—easily be chosen by a skilled person in this field and will be illustrated in the examples, without being limited hereto.

Of course, one skilled in this art will take care to select the above mentioned optional additional compound or compounds and/or their amounts such that the advantageous properties intrinsically associated with the combination in accordance with the invention are not, or not substantially, detrimentally affected by the envisaged addition or additions.

Suitable UV-filter substance to be incorporated into the topical compositions according to the present invention are conventional UVA and/or UVB and/or broad spectrum UV-filter substances known to be added into topical compositions such as cosmetic or dermatological sun care products. Such UV-filter substances comprise all groups which absorb light in the range of wavelengths 400 nm to 320 nm (UVA) and 320 nm to 280 nm (UVB) or of even shorter wavelengths (UVC) and which are or can be used as cosmetically acceptable UV-filter substances. Such UV-filter substances are e.g. listed in the CTFA Cosmetic ingredient Handbook or "The Encyclopedia of Ultraviolet Filters" (ISBN: 978-1-932633-25-2) by Nadim A. Shaath.

Suitable UV-filter substances may be organic or inorganic compounds. Exemplary organic UV-filter substances encompass e.g. acrylates such as e.g. 2-ethylhexyl 2-cyano-3,3-diphenylacrylate (octocrylene, PARSOL® 340), ethyl 2-cyano-3,3-diphenylacrylate; Camphor derivatives such as e.g. 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, terephthalylidene dicamphor sulfonic acid (Mexoryl® SX); Cinnamate derivatives such as e.g. ethylhexyl methoxycinnamate (PARSOL® MCX), ethoxyethyl methoxycinnamate, isoamyl methoxycinnamate as well as cinnamic acid derivatives bond to siloxanes; p-Aminobenzoic acid derivatives such as e.g. p-aminobenzoic acid, 2-ethylhexyl p-dimethylaminobenzoate, N-oxypropylenated ethyl p-aminobenzoate, glyceryl p-aminobenzoate; Benzophenones such as e.g. benzophenone-3, benzophenone-4,2,2',4,4'-tetrahydroxy-benzophenone, 2,2'-dihydroxy-4,4'-dimethoxybenzophenone; Esters of benzalmalonic acid such as e.g. di-(2-ethylhexyl) 4-methoxybenzalmalonate; Organosiloxane compounds carrying chromophore groups such as e.g. polysilicones-15 (PARSOL® SLX), drometrizole trisiloxane (Mexoryl® XL); Imidazole derivatives such as e.g. 2-phenyl benzimidazole sulfonic acid (PARSOL® HS) and salts thereof such as e.g. sodium- or potassium salts, ammonium salts, morpholine salts, salts of primary, sec. and tert. amines like monoethanolamine salts, diethanolamine salts; Salicylate derivatives such as e.g. isopropylbenzyl salicylate, benzyl salicylate, butyl salicylate, ethylhexyl salicylate (PARSOL® EHS, Neo Heliopan® OS), isooctyl salicylate or homomenthyl salicylate (homosalate, PARSOL® HMS, Neo Heliopan® HMS); Triazine derivatives such as e.g. ethylhexyl triazone (Uvinul® T-150), diethylhexyl butamido triazone (Uvasorb® HEB), bis-ethylhexyloxyphenol methoxyphenyl triazine (Tinosorb® S), 2,4,6-tris([1,1'-Biphenyl]-4-yl)-1,3,5-triazine (Tris Biphenyl Triazine, Tinosorb A2B); Benzotriazole derivatives such as e.g. 2,2'-methylene-bis-(6-(2H-benzotriazole-2-yl)-4-(1,1,3,3,-tetramethylbutyl)-phenol (Tinosorb® M); Encapsulated UV-filters such as e.g. encapsulated ethylhexyl methoxycinnamate (Eusolex® UV-pearls) or microcapsules loaded with UV-filters as e.g. dislosed in EP 1471995; Dibenzoylmethane derivatives such as e.g. 4-tert.-butyl-4'-methoxydibenzoyl-methane (PARSOL® 1789), dimethoxydibenzoylmethane, isopropyldibenzoylmethane; Phenylene-1,4-bis-benzimidazolsulfonic acids or salts such as e.g. 2,2-(1,4-phenylene)bis-(1H-benzimidazol-4,6-disulfonic acid) (Neoheliopan AP); Amino substituted hydroxybenzophenones such as e.g. 2-(4-diethylamino-2-hydroxy-benzoyl)-benzoic acid hexylester (Aminobenzophenon, Uvinul® A Plus); Benzoxazol-derivatives such as e.g. 2,4-bis-[5-1(dimethylpropyl)benzoxazol-2-yl-(4-phenyl)-imino]-6-(2-ethylhexyl)-imino-1,3,5-triazine (Uvasorb® K2A); Inorganic UV-filter substances encompass pigments such as e.g. microparticulated Zink oxide or Titanium dioxide (e.g. commercially available as PARSOL® TX) The term "microparticulated" refers to a particle size from about 5 nm to about 200 nm, particularly from about 15 nm to about 100 nm. The particles may also be coated by other metal oxides such as e.g. aluminum or zirconium oxides or by organic coatings such as e.g. polyols, methicone, aluminum stearate, alkyl silane. Such coatings are well known in the art.

In order to enhance the photostability of sun care products it may be desirable to add a photostabilizer. Exemplary photostabilizers known to a skilled person in the art encompass e.g. 3,3-diphenylacrylate derivatives such as e.g. octocrylene (PARSOL® 340) or Polyester-8 (Polycrylene®); Benzylidene camphor derivatives such as e.g. 4-methyl benzylidene camphor (PARSOL® 5000); Benzalmalonate derivatives such as e.g. polysilicones-15 (PARSOL® SLX) or diethylhexyl syringylidene malonate (Oxynex ST liquid); Dialkyl naphthalates such as diethylhexyl naphthalate (Corapan TQ) without being limited thereto. An overview on further stabilizers is e.g. given in 'SPF Boosters & Photostability of Ultraviolet Filters', HAPPI, October 2007, p. 77-83 which is included herein by reference. The photostabilizers are generally used in an amount of 0.05 to 10 wt.-% with respect to the total weigh of the topical composition.

Generally, the amount of each UV-filter substance in the topical compositions according to the invention is selected in the range of about 0.1 to 10 wt.-%, preferably in the range of about 0.2 to 10 wt.-%, most preferably in the range of about 0.5 to 10 wt.-%, based on the total weight of the topical composition.

The total amount of UVA-filter substance(s), in particular of butyl methoxydibenzoylmethane, in the topical compositions according to the invention is preferable selected in the range of about 0.5 to 8 wt.-%, in particular in the range of about 1 to 6 wt.-%, most particular in the range of about 1 to 5 wt.-%, based on the total weight of the topical composition.

The total amount of UV-filter substances in the topical compositions according to the invention is preferably in the range of about 1 to 40 wt.-%, preferably in the range of about 5 to 30 wt.-%, in particular in the range of 8 to 30 wt.-%, based on the total weight of the topical composition.

Preferred UVB-filter substances according to the invention encompass polysilicones-15, phenylbenzimidazol sulfonic acid, octocrylene, ethylhexyl methoxycinnamate, ethyl hexylsalicylate and/or homosalate.

Preferred broadband UV-filter substances according to the invention encompass unsymmetrical s-triazine derivatives such 2,4-Bis-{[4-(2-ethyl-hexyloxy)-2-hydroxy]-phenyl}-6-(4-methoxyphenyl)-1,3,5-triazine or 2,4,6-Tris([1,1'-Biphenyl]-4-yl)-1,3,5-Triazine (Tris Biphenyl Triazine, Tinosorb A2B), certain benzophenones such as e.g. 2-Hydroxy-4-methoxy-benzophenon, 2,2'-Methylen-bis-(6-(2H-benzotriazol-2-yl)-4-(1,1,3,3-tetramethyl-butyl)-phenol), and/or titanium dioxide.

The preferred UVA-filter substance according to the invention is butyl methoxydibenzoylmethane. Preferably, butyl methoxydibenzoylmethane is the only UVA-filter substance in the topical compositions according to the invention.

In a particular preferred embodiment, the composition comprise at least one UV-filter substance selected from the group consisting of butyl methoxydibenzoylmethane, octocrylene, homosalate and ethylhexyl salate as well as mixtures thereof. In a particular advantageous embodiment all of butyl methoxydibenzoylmethane, octocrylene, homosalate and ethylhexyl salate are present in the compositions according to the present invention.

The topical cosmetic compositions of the invention can also contain usual cosmetic adjuvants and additives, such as preservatives/antioxidants, fatty substances/oils, water, organic solvents, silicones, thickeners, softeners, emulsifiers, sunscreens, antifoaming agents, moisturizers, aesthetic components such as fragrances, surfactants, fillers, sequestering agents, anionic, cationic, nonionic or amphoteric polymers or mixtures thereof, propellants, acidifying or basifying agents, dyes, colorings/colorants, abrasives, absorbents, essential oils, skin sensates, astringents, antifoaming agents, pigments or nanopigments, e.g. those suited for providing a photoprotective effect by physically blocking out ultraviolet radiation, or any other ingredients usually formulated into cosmetic compositions. Such cosmetic ingredients commonly used in the skin care industry, which are suitable for use in the compositions of the present invention are e.g. described in the CTFA Cosmetic Ingredient Handbook, Second Edition (1992) without being limited thereto.

The necessary amounts of the cosmetic and dermatological adjuvants and additives can—based on the desired product—easily be chosen by a skilled person in this field and will be illustrated in the examples, without being limited hereto.

Of course, one skilled in this art will take care to select the above mentioned optional additional compound or compounds and/or their amounts such that the advantageous properties intrinsically associated with the combination in accordance with the invention are not, or not substantially, detrimentally affected by the envisaged addition or additions.

The topical compositions according to the present invention preferably have a viscosity of at least 1000 mPs (determined by TA Instruments AR 550, Shear rate 1 s$^{-1}$, 25° C., plate SST ST 40 mm), preferably in the range of 2000-15000 mPas such as in the range of 5000-13000 mPas.

The topical compositions according to the invention preferably have a pH in the range of 3-10, more preferably in the range of pH of 4-8, most preferred in the range of pH 4-7.

The following examples are provided to further illustrate the compositions and effects of the present invention. These examples are illustrative only and are not intended to limit the scope of the invention in any way.

EXAMPLE 1

Various formulations using different emulsifiers (anionic (Ref) and nonionic (Inv)) have been prepared as outlined in Table 1 and 2. Initially, no crystals have been observed in any of the formulations by microscopy analysis. Then the formulations have been stored at room temperature and repeatedly been microscopically analyzed for re-crystallization of 10-hydroxystearic acid up to 3 months. The results thereof are outlined in Table 2.

TABLE 1

| | INCI | Wt.-% |
|---|---|---|
| A | Butyl Methoxydibenzoyl Methane | 3.0 |
| | Octocrylene | 2.7 |
| | Homosalate | 5.0 |

TABLE 1-continued

| | INCI | Wt.-% |
|---|---|---|
| | Ethylhexyl Salicylate | 5.0 |
| | $C_{12-15}$ Alkyl Benzoate | 5.0 |
| | Cetearyl Alcohol | 2.0 |
| | Behenyl Alcohol | 1.0 |
| | BHT | 0.1 |
| | Acrylates/$C_{10-30}$ Alkyl Acrylate Crosspolymer | 0.1 |
| | 10-Hydroxystearic Acid | 1.0 |
| | Emulsifier | See table 2 |
| | Stearic Acid | |
| B | Xanthan Gum | 0.2 |
| | Disodium EDTA | 0.1 |
| | Butylene Glycol | 2.0 |
| | Sodium Hydroxide | 0.1 |
| | Aqua | Ad 100 |
| C | Phenoxyethanol; Ethylhexylglycerin | 1.0 |

Preparation Procedure

1st Heat part A to 90° C. and part B to 80° C.
$2^{nd}$ Combine part A and B and homogenize 1 minute at 10.000 rpm.
$3^{rd}$ Cool down while stirring.
$4^{th}$ Add part C at 35° C. while stirring.
$5^{th}$ At last, Cool down to RT while stirring.

TABLE 2

| | Emulsifier | wt.-% | microscopy aspect crystallization after |
|---|---|---|---|
| Ref | Potassium Cetyl phosphate | 2.0 | 2 weeks |
| Ref | Stearic Acid | 8.0 | 2 weeks |
| Ref | $C_{20-22}$ Alkyl Phosphate (And) $C_{20-22}$ Alcohols | 2.0 | 2 weeks |
| Ref | Glyceryl Stearate Citrate | 2.0 | 2 weeks |
| Ref | Disodium Cetearyl Sulfosuccinate | 1.0 | 2 weeks |
| Inv | Polyglyceryl-3 Methylglucose Distearate | 3.0 | 6 weeks |
| Inv | Cetearyl Olivate (and) Sorbitan Olivate | 4.0 | 12 weeks |
| Inv | Cetearyl Glucoside | 1.5 | 6 weeks |
| Inv | Methyl Glucose Sesquistearate | 2.5 | 6 weeks |
| Inv | PEG-100 Stearate (and) Glyceryl Stearate | 3.5 | No crystals after 3 months |
| Inv | Steareth-2 (and) Steareth-21 | 2.5/1.0 | No crystals after 3 months |

As can be retrieved from Table 2, the use of a nonionic emulsifier significantly retards or even inhibits the recrystallization of 10-hydroxystearic acid in a topical composition.

EXAMPLE 2

A formulation comprising a nonionic, PEG-based emulsifier (PEG-40 Stearate) and an anionic emulsifier (stearic acid) as outlined in table 3 has been prepared.

This formulation also did not result in any crystal formation, even after 3 months.

TABLE 3

| INCI | Wt.-% |
|---|---|
| BHT | 0.1 |
| 10-Hydroxystearic Acid | 1.0 |
| Stearic Acid | 17.0 |
| Isopropyl Myristate | 10.0 |
| PEG-40 Stearate | 5.0 |
| Stearyl Alcohol | 3.0 |
| Sorbic Acid | 0.2 |

TABLE 3-continued

| INCI | Wt.-% |
|---|---|
| Xanthan Gum | 0.3 |
| Aqua | Ad 100 |
| microscopy aspect crystallization after: | No crystals after 3 months |

The invention claimed is:

1. A topical composition comprising:
   0.001 to 5 wt. %, based on the total weight of the composition, of 10-hydroxystearic acid or a salt thereof,
   at least one nonionic emulsifier, and
   a co-emulsifier selected from the group consisting of nonionic solid fatty alcohols having from 12 to 22 carbon atoms and mixtures thereof, wherein
   the topical composition is an oil/water (O/W) emulsion comprising at least 10 wt. % of an oily phase and at least 50 wt. % of an aqueous phase, based on total weight of the composition,
   with the proviso that the composition is free of isobutylparabene.

2. The topical composition according to claim 1, which is also free of a cooling agent and/or an exothermic agent.

3. The topical composition according to claim 1, wherein the nonionic emulsifier is present in an amount of 0.1 to 7 wt. %, based on the total weight of the composition.

4. The topical composition according to claim 1, wherein the 10-hydroxystearic acid is (R)-10-hydroxystearic acid.

5. The topical composition according to claim 1, wherein the at least one nonionic emulsifier is selected from the group consisting of esters of fatty alcohols, polyalkylenglycol alkyl ethers, polyalkyleneglycol fatty acid esters, glucoside alkyl ethers, alkyl glucose esters, glycerol alkyl esters, sorbitan fatty acid esters, block polymers of polyethylene glycol and block polymers of polypropylene glycol.

6. The topical composition according to claim 1, wherein the at least one nonionic emulsifier is selected from the group consisting of $C_{12}$-$C_{22}$-alkylester of $C_{12}$-$C_{22}$-alcohols, polyethylene glycol alkyl ethers, polyethylene glycol fatty acid esters, (polyglyceryl) alkylglucose alkyl esters, glycerol $C_{12}$-$C_{22}$ fatty acid esters and sorbitan mono fatty acid esters.

7. The topical composition according to claim 1, wherein the at least one nonionic emulsifier is selected from the group consisting of polyglycery 3 methylglucose distearate, cetearyl glucoside, methyl glucose sesquistearate, cetearyl olivate, sorbitan olivate, PEG-40 stearate, PEG-100 stearate, glyceryl stearate, steareth-2 and steareth-21.

8. The topical composition according to claim 1, wherein the co-emulsifier is selected from the group consisting of cetyl alcohol, behenyl alcohol, cetearyl alcohol and mixtures thereof.

9. The topical composition according to claim 1, wherein the co-emulsifier is present in an amount of 0.1 to 20 wt. %, based on the total weight of the composition.

10. The topical composition according to claim 1, wherein the composition comprises a preservative selected from the group consisting of phenoxyethanol, ethylhexylglycerin and mixtures thereof.

11. The topical composition according to claim 1, wherein the oily phase is present in an amount of less than 40 wt. % and the aqueous phase is present in an amount of at least 60 wt. %, based on total weight of the composition.

12. The topical composition according to claim 1, wherein the oily phase is present in an amount of less than 30 wt. % and the aqueous phase is present in an amount of at least 70 wt. %, based on total weight of the composition.

13. The topical composition according to claim 1, wherein the oily phase is present in an amount of 10-30 wt. % and the aqueous phase is present in an amount of 70-90 wt. %, based on total weight of the composition.

14. A method to retard or inhibit the re-crystallisation of 10-hydroxystearic acid or a salt thereof in an oil/water (O/W) topical composition comprising at least 10 wt. % of an oily phase and at least 50 wt. % of an aqueous phase, based on total weight of the composition, wherein the method comprises formulating 10-hydroxystearic acid or a salt thereof in the presence of at least one nonionic emulsifier and a co-emulsifier selected from the group consisting of nonionic solid fatty alcohols having from 12 to 22 carbon atoms and mixtures thereof in the absence of isobutylparabene.

15. The method according to claim 14, wherein the at least one nonionic emulsifier is selected from the group consisting of polyglycery 3 methylglucose distearate, cetearyl glucoside, cetearyl olivate, sorbitan olivate, methyl glucose sesquistearate, PEG-40 Stearate, PEG-100 stearate, glyceryl stearate, steareth-2 and steareth-21 and mixtures thereof.

16. The method according to claim 15, wherein the at least one nonionic emulsifier is selected from the group consisting of PEG-40 stearate, PEG-100 stearate, steareth-2 and steareth-21 and mixtures thereof.

17. The method according to claim 14, wherein the oily phase is present in an amount of less than 40 wt. % and the aqueous phase is present in an amount of at least 60 wt. %, based on total weight of the composition.

18. The method according to claim 14, wherein the oily phase is present in an amount of less than 30 wt. % and the aqueous phase is present in an amount of at least 70 wt. %, based on total weight of the composition.

19. The method according to claim 14, wherein the oily phase is present in an amount of 10-30 wt. % and the aqueous phase is present in an amount of 70-90 wt. %, based on total weight of the composition.

* * * * *